United States Patent [19]

Nakamura

[11] Patent Number: 4,538,290

[45] Date of Patent: Aug. 27, 1985

[54] APPARATUS FOR DETECTING AN ABNORMALITY IN PAPERLIKE MATERIAL

[75] Inventor: Yasushi Nakamura, Yokohama, Japan

[73] Assignee: Tokyo Shibaura Denki Kabushiki Kaisha, Kawasaki, Japan

[21] Appl. No.: 184,904

[22] Filed: Sep. 8, 1980

Related U.S. Application Data

[63] Continuation of Ser. No. 969,379, Dec. 14, 1978, abandoned.

[51] Int. Cl.³ .......................................... G01M 23/22
[52] U.S. Cl. ...................................... 378/44; 378/50; 378/86; 378/89
[58] Field of Search ...................... 378/86, 88, 44, 45, 378/48, 49, 50

[56] References Cited

U.S. PATENT DOCUMENTS 3,001,073  9/1961  Alexander ............................. 378/86
3,506,829  4/1970  Hannan ................................. 378/86

Primary Examiner—Craig E. Church
Attorney, Agent, or Firm—Oblon, Fisher, Spivak, McClelland & Maier

[57] ABSTRACT

An X-ray generating apparatus for detecting an abnormality in paperlike material, wherein the paperlike material is irradiated by X-rays and the secondary X-ray from the paperlike material is detected and compared against an X-ray emission standard to detect the abnormality in the paperlike material.

2 Claims, 19 Drawing Figures

APPARATUS FOR DETECTING AN ABNORMALITY IN PAPERLIKE MATERIAL

This is a continuation of application Ser. No. 969,379, filed Dec. 14, 1978, now abandoned.

BACKGROUND OF THE INVENTION

1. Field of the Invention

This invention relates to an apparatus for detecting an abnormality in a paperlike material, where the term "abnormality" herein refers to an irregularity in some characteristic or property, for example, an abnormality in thickness, sticking of a binding tape, double pile of the papers, false banknote and so on.

2. Discussion of the Prior Art

The prior art to which this invention is directed is described in Japanese Patent Publication (KOKOKU) No. 43-25448, publication date Nov. 2, 1968. This publication shows a bill or a check sorter, in which certain special radioactive elements are beforehand instilled in a bill or a check, and the bill or check is examined as to whether it is false or not by detecting the radiant energy from the radioactive elements. The prior art to examine the authenticity of a bill or check thus requires the introduction of special radioactive elements in the bill or check beforehand.

BRIEF SUMMARY OF INVENTION

Accordingly, it is an object of this invention to provide an improved apparatus for detecting an abnormality in paperlike material.

Another object of this invention is to provide an improved apparatus for detecting an abnormality in the thickness of a paperlike material.

A further object of the invention is to provide an improved sorter for running paperlike material.

Still another object of this invention is to provide an apparatus for detecting an abnormality in running paperlike material, regardless of the existence of printed patterns on the sheet or any stains in the sheet, without contacting the paperlike material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
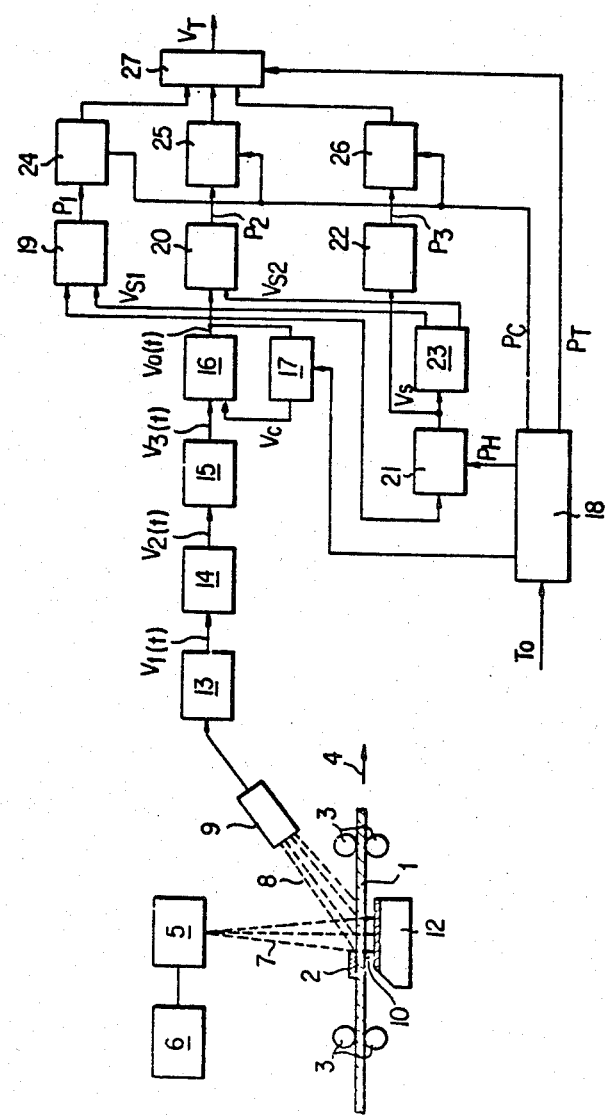
FIG. 1 is a schematic block diagram of a preferred embodiment of this invention.
Figure 2:
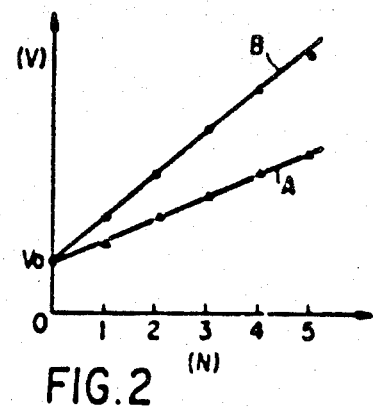
FIG. 2 is a graphical representation showing the Compton scattering X-ray intensity in relation to the numbers of sheets.

Referring now to the drawings, wherein like reference numerals designate identical or corresponding parts throughout the several views, and more particularly to FIG. 1 thereof, the examined paperlike material (1) is conveyed by the conveying means, such as conveying roller (3) with the constant speed in the arrowed direction (4) as shown. The figure shows a binding tape (2) mistakenly stuck to the paperlike material (1). The paperlike material (1) is irradiated in a prefixed area by X-ray (7), which is generated by applying a high voltage source (6) to the X-ray tube (5) for example, a molybdenum X-ray tube. When the paperlike material which contains elemental atoms of Carbon (C), Hydrogen (H), Oxygen (O) is irradiated by X-rays, Compton scattering occurs conspicuously. The intensity of this Compton scattering X-ray is shown in FIG. 2 in which N denotes the numbers of sheets and V denotes the intensity of the scattering X-ray. In FIG. 2, curve A and curve B denote the results of piling up the sheets of paperlike material, where the sheets have the thickness of 50 $\mu$m and 100 $\mu$m, respectively. From these curves, it is seen that linearity of the Compton scattering X-ray intensity to the total thickness of the paperlike materials is adequate at least in the thickness range of 50 to 500 $\mu$m.

Returning to FIG. 1, scattered X-ray (8) which is generated by the irradiation of the X-ray (7) to the paperlike material, is detected by the usual X-ray detecting tube. In the path of X-rays which have penetrated the paperlike material is situated a standard scattering member (10) which is disposed on an X-ray absorbing plate (12). The X-ray absorbing plate (12) is used for the purpose of absorbing the X-rays which have penetrated the scattering member (10). Although it is not shown in the drawing, X-ray tube (5), X-ray detecting tube (9) and X-ray irradiating areas are surrounded by a protective cover to prevent leakage of X-rays.

The standard scattering member (10) provides a constant intensity value (Vo in FIG. 2) to the X-ray detecting tube (9) and is used as a standard signal (11) for a later discussed automatic gain control circuit (16). This standard scattering X-ray (11) is also generated by the existence of the paperlike material, but the intensity is constant and presents no problem in handling the signals. Scattered X-ray (8), (11) detected by X-ray detecting tube (9) are respectively converted to electrical pulse signals which are spaced in proportion to their intensities. These electrical pulse signals are amplified to a suitable voltage level, namely $V_1(t)$, by the preamplifier (13). The output $V_1(t)$ is then applied to a discriminator (14), which selects only the scattered X-rays from both the paperlike material and the standard scattering member (10) by setting up the uppermost pulse wave height value and the lowermost pulse wave height value in advance and passes the signal $V_1(t)$ only when $V_1(t)$ falls in between these two values. As a discriminator, a well known pulse wave height analyzer is used. In this embodiment a molybdenum X-ray tube is used, and the molybdenum characteristic X-ray ($\sim$0.7 A) is intensive. It is most desirable to detect the Compton scattering of the molybdenum characteristic X-ray for the improvement of S/N ratio and the miniaturization of the X-ray tube.

When the examined paperlike material does not reach the X-ray irradiating area, then the output pulse signal of the discriminator (14) is $v_2(t)$ which corresponds to the standard scattering X-ray (11). This pulse signal $v_2(t)$ is supplied to the rectifying circuit (15) which converts the signal to the direct current signal $v_3(t)$. This output $v_3(t)$ is supplied to the automatic gain control circuit (16) as a standard input. The output value $V_0(t)$ of this automatic gain control circuit (16) is set to the constant value $V_0$ when the standard signal $v_3(t)$ is applied. This setting is done by the control signal $V_c$ of the signal level detecting circuit (17). By setting the gain of the automatic gain control circuit (16) one can neglect, for example, the characteristic variation of the X-ray tube (9) or the variation of detecting sensitivities of the X-ray detecting means, which enables the accurate measurement of the examined material.

Nextly, when the paperlike material (1) reaches the X-ray irradiating area, control pulse signal $P_A$ is generated by control pulse generating circuit (18). This pulse $P_A$ is generated, for example, by basing on the edge detecting signal $T_o$ which is generated by detecting the edge of the paperlike material (1) by an opto-electronic switch (not shown). Upon detecting the existence of the paperlike material in the X-ray irradiating area, the $P_A$ level is set to "1", and this control pulse signal $P_A$ is supplied to the signal level detecting circuit (17). When this control pulse signal $P_A$ is supplied to the signal level detecting circuit (17), the signal level detecting circuit holds the control signal $V_c$, and the gain control loop thereby becomes open. In this state, the output signal $v_2(t)$, which corresponds to the Compton scattering X-ray (8) from the paperlike material (1), is obtained. The output $v_2(t)$ is rectified by the rectifying circuit (15), and then supplied to the automatic gain control circuit (16).

At this time, the output $V_o(t)$ varies according to the thickness of the paperlike material. This output $V_o(t)$ is supplied to later mentioned first and second Schmitt circuit (19), (20), and also to the samplehold circuit (21). This circuit (21) samples the output $V_0(t)$ synchronous with the timing pulse signal ($P_H$) and holds the analog value. The timing signal ($P_H$) is generated simultaneously by the control pulse generating circuit (18), when the edge of the paperlike material (1) covers the width portion of the X-ray irradiating area. Therefore in the samplehold circuit (21), thickness signal $V_s$ which corresponds to the edge of the paperlike material is held. This signal $V_s$ is supplied to both the third Schmitt circuit (22) and Schmitt level signal generating circuit (23). This Schmitt level signal generating circuit (23) generates two Schmitt level signals $V_{s1}$, $V_{s2}$ based on the thickness signal $V_s$. These signals are supplied to the first and second Schmitt circuits (19) and (20). Here the Schmitt level signals $V_{s1}$ and $V_{s2}$ have the following relations, namely, $V_{s1} = V_s - dV$, $V_{s2} = V_s - dV$. $V_{s1}$ the level to detect an excess thickness of the paperlike material (1) and $V_{s2}$ is the level to detect a shortage in thickness of the paperlike material (1) in comparison with the standard thickness. First Schmitt circuit (19) generates output signal $P_1$ which has the value of "1", when the output $V_o(t)$ of the aforementioned variable gain control circuit exceeds the Schmitt level signal $V_{s1}$. Second Schmitt circuit (20) generates output signal $P_2$ which has the value of "1", when the output $V_o(t)$ of the variable gain control circuit is less than the Schmitt level signal $V_{s2}$. Third Schmitt circuit (22) has the upper and lower limits of $V_{SH}$, $V_{SL}$, and when the samplehold signal $V_s$ falls between these two values, it generates signal $P_3$ which has the output value of "1". These limits $V_{SH}$, $V_{SL}$ correspond to the allowable thickness range of the standard thickness. Thus, for example, when two papers are piled, it goes beyond these limits. The outputs $P_1$, $P_2$, $P_3$ of these Schmitt circuits (19), (20), (21) are memorized in the 1 bit memories, for example, flip-flop memories (24), (25), (26). These memories are cleared by timing signal $P_c$ just before the paperlike material (1) reaches the X-ray irradiating area. The outputs of these memories (24), (25), (26) are supplied to the logic circuit (27). This logic circuit (27) generates a total judging or discriminating signal $V_T$ synchronizing the timing signal $P_T$ just after the paperlike material (1) leaves the X-ray irradiating area. This discrimination is done on the signals of the Schmitt circuits (19), (20), (21). The timing signals $P_C$ and $P_T$ are generated by the control pulse generating circuit (18) to which edge detecting signal input $T_0$ is supplied.

Figure 3:
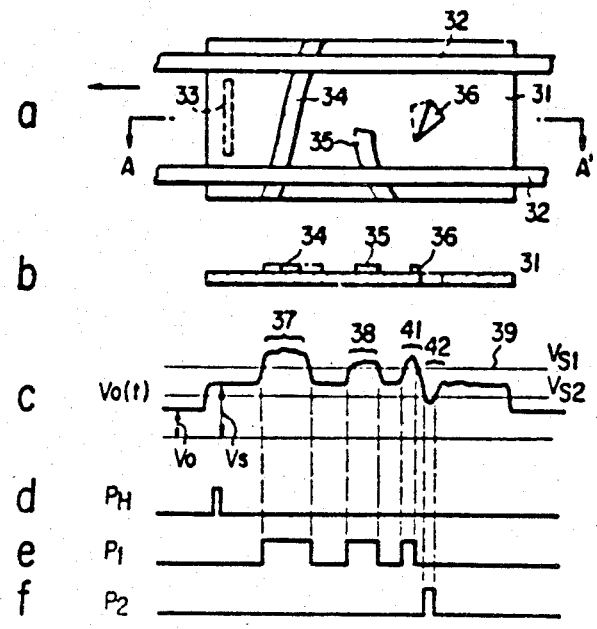
FIG. 3(a) is a plan view showing one state of the examined paperlike materials.
FIG. 3(b) is a sectional view along the A—A' line in FIG. 3(a)
FIG. 3(c) is a graphical representation showing the output of an automatic gain control circuit.
FIG. 3(d) is a graphical representation showing the samplehold timing signal.
FIGS. 3(e) and (f) are graphical representations, respectively showing the outputs P1, P2 of Schmitt Trigger Circuit (19) and (20)

Referring now to FIG. 3, an example of the detection of an abnormality in thickness according to this invention is explained. As is shown in FIG. 3(a) printed paperlike material (31) is conveyed in the arrowed direction by the conveying belts (32). The thickness of the paperlike material is for example 100 to 200 µm. The print layer thickness is 5 to 10 µm. The paperlike material (31) is irradiated when it reaches the X-ray irradiation area (33) which is shown by dotted line. FIG. 3(a) also shows the existence of the abnormality, such as sticking of the binding tapes (34), (35) and the tear hole (36). In FIG. 3(b), a sectional view of the paperlike material is shown. When the paperlike material (31) passes the X-ray irradiating area (33) the output $V_0(t)$ of the variable gain control circuit (16) becomes like the signal shown in FIG. 3(c) in accordance with the Compton scattering X-ray intensity. Without the existence of the paperlike material the output is $V_0$, and when the edge of the paperlike material reaches the area (33) it becomes $V_S$. When the binding tape (34) covers all the X-ray irradiating area (33), then the resultant output (37) is obtained in proportion to the thickness of the tape (34). When the binding tape (35) covers a small area in the X-ray irradiating area, then the output (38) is obtained, which is not proportional to the thickness of the tape (35). In FIG. 3(c), the designation (41) corresponds to the turn over of the paper and (42) corresponds to the hole portion of the paper. By setting the Schmitt level to $V_{S1}$, $V_{S2}$ shown in FIG. 3(c), (39) and (40), the output pulse $P_1$ and $P_2$ of the first and second Schmitt circuits (19) and (20) are obtained as shown in FIGS. 3(e) and (f). In this embodiment output $P_1$ has three pulses, but the memory (24) can be set by the first pulse.

To supplement the above described explanation, when the edge portion of the paperlike material has an abnormality, for example, the binding tape is stuck thereto, then the signal $V_S$ becomes the standard, which is in fact in excess to the normal thickness, and the normal thickness portion is discriminated as short of thickness. But the existence of the abnormality in thickness is detected, and it presents no practical problem. In other words, in the event of the existence of different thickness portions in the paperlike material, one can detect it by the first and second Schmitt circuits.

When, for example, two papers are folded or totally the thickness of the paperlike material is different, then there is no thickness change throughout the paper and one cannot detect the abnormality by the first and second Schmitt circuit. But in this case $V_S$ becomes beyond the range of $V_{SL}$ and $V_{SH}$ and so, by means of third Schmitt circuit (22), one can detect the abnormality in thickness.

Moreover by using the X-ray standard scattering member (10) and the automatic gain control circuit (16), even if the intensity of the X-ray tube or the sensitivity of the detection tube varies, one can nevertheless obtain a very precise detection in thickness not only of the same paperlike material but also of the different kinds of paperlike materials.

As previously mentioned, the print layer thickness is small enough that X-ray scattering from the print layer is negligible compared to that from the paperlike material. The existence of the print pattern and/or a stain do not affect the thickness detection.

Instead of using the X-ray tubes as an X-ray source, one can use a radioisotope source. Also to detect the Compton scattering X-ray one can use a dispersion method by utilizing a spectrocrystal approach, instead of the non-dispersion method described above.

Another embodiment of this invention will be explained referring to FIGS. 4–7. In this embodiment, a scattered fluorescent X-ray, which is also the secondary X-ray, from the examined paperlike material, is detected.

Figure 4:
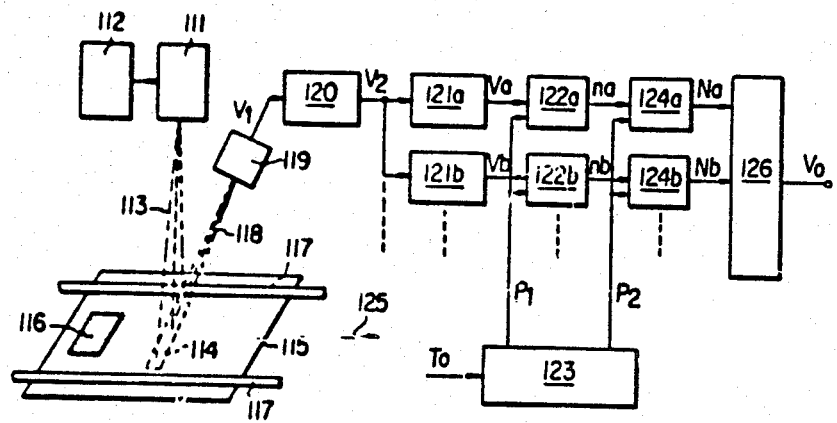
FIG. 4 is a schematic block diagram of another embodiment of this invention.

As is shown in FIG. 4, a paperlike material, for example, postcard (115) is irradiated by an X-ray (113) which is generated by applying a high voltage power from the power source (112) to the X-ray generating tube (111). An X-ray irradiating area is shown by dotted line (114). On the postcard, poststamp (116) is stuck. The postcard is conveyed with a constant speed in the arrowed direction (125) by the conveying belts (117). When the paperlike material contains metal atoms, for example, Zn, Sn, then the fluorescent X-ray (118) is generated. This fluoresent X-ray (118) has the following relation, namely $E = hc/\lambda$ (where E=Energy, h=Planck constant $\lambda$=wave length, c=electro-magnetic wave speed). Wave length ($\lambda$) of the fluorescent X-ray (118) depends on the sort of contained atoms, and the intensity thereof is proportional to the quantity of the atoms. Nextly, by detecting the X-ray and converting it to an electric signal one can obtain pulse signals which depend on the wave length of the X-ray. By measuring the pulse wave height, the sort of atoms contained in the paperlike material is discriminated. Also by counting the number of pulses, one can tell the quantity of atoms.

This fluorescent X-ray (118) is detected by X-ray detecting tube (119), which converts the X-ray detected by the the X-ray detecting tube (119) to an electric pulse signal $V_1$. This signal $V_1$ is supplied to the preamplifier (120). This preamplifier (120) amplifies the signal $V_1$ to signal $V_2$ and supplies it to a bank of discriminators such as (121-a), (121-b), ..., each of which is used to detect an X-ray scattering characteristic of a specific element.

Discriminators (121-a), (121-b) for example, are used to detect a fluorescent X-ray from Zn and Cu, respectively. Each discriminator has its own upper and lower limits concerning the pulse wave height. When the postcard contains Zn, then from the pulse signal $V_2$ only the pulse signal from Zn falls between the upper and lower limits of the associated discriminator, and passes the discriminator. Thus, the output pulse Va is obtained.

It is also the case, when, for example, the print layer on the postcard (116) contains Cu, that the second discriminator (121-b) produces an output indicative thereof, and so on.

The output pulse Va is supplied to the counter (122-a), which is controlled by counter clear pulse $P_1$ generated by control pulse generating circuit (123) and which counts the output pulse Va with a predetermined timing. Counted value ($n_a$) is then latched by the circuit (124-a). This latch timing is controlled by the latch timing pulse $P_2$ which is generated by the control pulse generating circuit (123). $P_1$ based on the existence of edge detection signal To, is generated by detecting the edge of the postcard (115) by means of an opto-electric switch (not shown). Thus, just before the poststamp (116) reaches the X-ray irradiating area (114), the signal $P_1$ is generated. Pulse $P_2$ is generated just after the poststamp (116) leaves the X-ray irradiating area (114).

Counted value $N_a$ which is latched in the circuit (124-a) corresponds to the fluorescent X-ray intensity, and it is supplied to the comparison judgement logic circuit (126). This comparison judgement logic circuit (126) comprises the digital comparator and compares $N_a$ of the examined object and $N_{oa}$ of the correct sample poststamp which is recorded beforehand. When $N_a$ falls within the allowance of the correct poststamp, then circuit (126) generates an output logic signal "1", if not an output logic signal "0".

Figure 5:
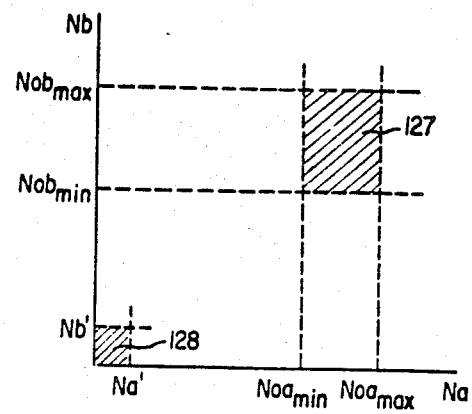
FIG. 5 is a diagram showing a range of allowance.

In the case when the paperlike material contains a plurality of atoms which are to be detected, discriminator, counter, and latch circuits may be provided in parallel as is shown in FIG. 4. More precisely, for the case where the poststamp paper contains element A (for example Zn), and the print ink of the poststamp contains element B (for example Cu), as shown, element A is detected by (121-a), (122-a), (124-a) and element B is detected by (121-b), (122-b), (124-b). In the comparison judgement logic circuit (126), fluorescent X-ray Intensity $N_a$, $N_b$ are compared with the right value of $N_{0a}$, $N_{0b}$, respectively. As is shown in FIG. 5 there exists the allowance range namely $N_{0a}$ max, $N_{0a}$ min and $N_{0b}$ max, $N_{0b}$ min. If both $N_a$ and $N_b$ falls within the hatched region (127), then an output logic signal "1" is generated. If either one of $N_a$ and $N_b$ falls beyond the region (127), an output logic signal "0" is generated. If the poststamp contains neither element Zn nor element Cu, then the outputs of the latch circuits (124-a) and (124-b) are negligibly small in consideration of the noise component of the detection system, namely $N_a'$, $N_b'$ (128) as shown in FIG. 5. Thus the comparison judgement logic circuit outputs a "0" logic signal. By replacing the counters, latch circuits and digital comparator by an integral circuit, samplehold circuit and analog comparator, respectively, one can obtain the same function as is described in FIG. 4.

Figure 6:
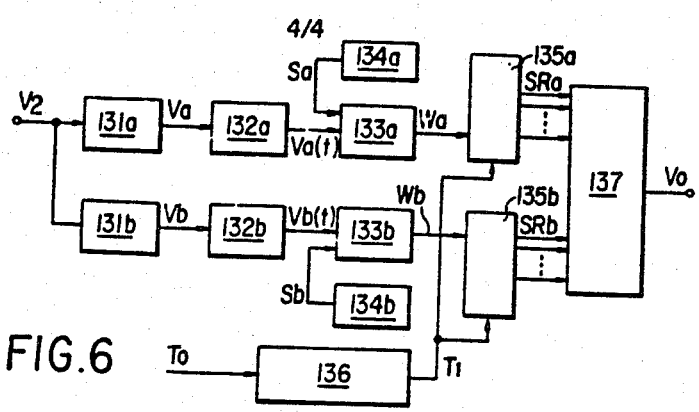
FIG. 6 is a schematic block diagram of a modified embodiment of this invention.
Figure 7:
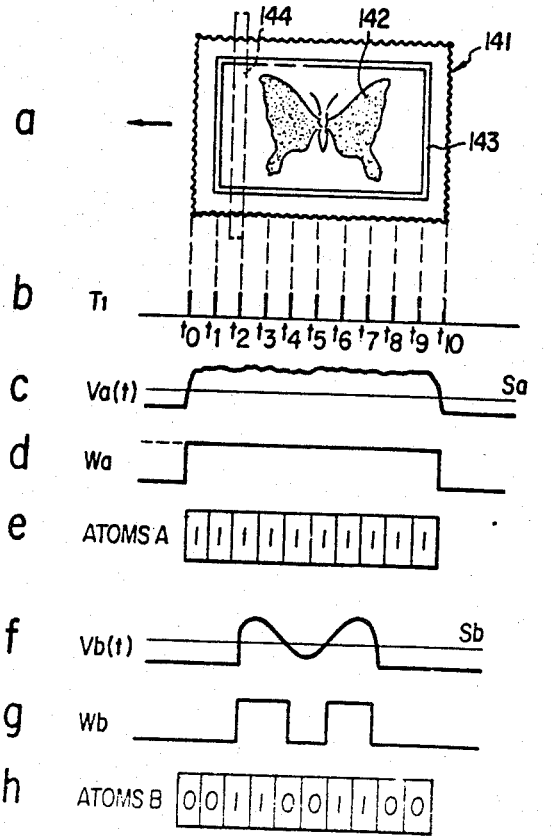
FIGS. 7(a) to (h) are the schematic representations explaining the specified example of this invention.

Now referring to FIG. 6 and FIG. 7, a somewhat modified embodiment is explained. In this embodiment the printed object, for example, the poststamp is subdivided and the existence of a specified element is detected for each subdivided area, thus enabling an accurate judgement of the authenticity of the printed object. Besides this type of judgement, one can also tell the sort of printed object which results from the different print patterns. As is shown in FIG. 6, output signal $V_2$ from the X-ray detecting tube is supplied to discriminators (131-a), (131-b) which function just the same as (121-a), (121-b) in FIG. 4. The output $V_a$, $V_b$ of the discriminators (131-a), (131-b) is now supplied to the rectifying circuits (132-a), (132-b) and converted to analog signal $v_a(t)$, $v_b(t)$. By choosing the suitable time constant in these rectifying circuits (132-a), (132-b), the output signals $v_a(t)$, $v_b(t)$ become analog voltage signals showing the time change of the fluorescent X-ray intensity. These output signals $v_a(t)$, $v_b(t)$ are supplied to the Schmitt circuits (133-a), (133-b) and compared with the prefixed value $S_a$, $S_b$ which are fixed by Schmitt level fixers (134-a), (134-b). The Schmitt circuits (133-a), (133-b) then output the signals $W_a$, $W_b$ respectively. When the output signals $v_a(t)$, $v_b(t)$ are larger than the fixed Schmitt level $S_a$, $S_b$, respectively, then the signals $W_a$, $W_b$ are at the logic signal "1", and when they are smaller, $W_a$, $W_b$ are at the logic signal "0". The output signals $W_a$, $W_b$ are supplied to n-stage shift registers (135-a), (135-b) and stored in the shift registers in accordance with the timing signal $T_1$ which is generated by the control pulse generating circuit (136). This timing signal $T_1$ is generated based on the edge detection signal $T_o$ (as is explained referring to FIG. 4) and a plurality of timing signals are generated when the whole poststamp passes the X-ray irradiating area. In the shift registers (135-a), (135-b) the outputs $W_a$, $W_b$ are stored when the timing signal $T_1$ is supplied.

The stored bit pattern is then supplied to the comparison judgement logic circuit (137), and compared with the bit pattern of the right poststamp. The judgement signal $V_o$ is chosen such that when both patterns coincide, then the output is "1", and when not, then the output is "0".

To explain more in detail, FIG. 7(a) to FIG. 7(h) are provided. In FIG. 7(a) poststamp (141) with the printed picture to butterfly (142) and also the printed outer frame (143) is shown. Poststamp paper (141) contains element A, the printed (checked) picture of the butterfly (143) contains element B, and the printed outer frame (143) contains element C. (In this embodiment the element C is not detected.) Numeral 144 shows the X-ray irradiating area and when the examined object, for example, the poststamp passes the area (144), fluorescent X-ray is generated.

As shown in FIG. 7(b) the poststamp is subdivided into ten regions and timing signal $T_1$ is generated at each timing $t_0, t_1, t_2, \ldots, t_{10}$. When at each of these timings the detection signal of fluorescent X-ray $V_2$ is generated, then it is supplied to discriminators (131-a), (131-b) and then to the rectifying circuits (132-a), (132-b). Outputs $v_a(t)$ and $v_b(t)$ are obtained as shown in FIG. 7(c) and FIG. 7(f). These outputs $v_a(t)$, $v_b(t)$ are compared with the Schmitt level $S_a$, $S_b$ respectively, and the outputs $W_a$, $W_b$ are produced as shown in FIG. 7(d) and FIG. 7(g).

Element A is contained throughout the whole poststamp paper (141) and so $v_a(t)$ is always beyond the Schmitt level $S_a$. Thus in the shift register (135-a), the bit pattern of element A becomes as shown in FIG. 7(e) in which all bits are "1". On the other hand element B is contained in the checked part of 142 and so $v_b(t)$ surpasses the Schmitt level $S_b$ at the timing $t_3$, $t_4$ and $t_7$, $t_8$. Thus the bit pattern of element B is as shown in FIG. 7(h), namely, the third, fourth, seventh and eighth bits are "1" and the rest are "0". In the case where all the bits in the pattern coincide with those of the right poststamp, judgement signal $V_0$ becomes "1".

In this way, by subdividing the examined object into several regions and detecting the existence of special atoms in each region, more accurate judgement is possible. As is clear from the embodiment, this invention is not only useful for the discrimination of the rightness or integrity of the examined object, but also is applicable to sorting of different poststamps, printed materials like bills or checks, and so on. Printed matters are of course not restricted to the poststamp, but applicable to other printed things.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for examining a piece of paper having a pattern printed thereon, comprising:
    means for transferring said piece of paper;
    means for irradiating X-rays on said piece of paper transferred by said transferring means;
    detecting means for detecting fluorescent X-rays scattered from said printed pattern on said paper;
    subdividing means for subdividing said paper and the pattern located thereon into a plurality of areas;
    a plurality of discriminator means each connected to said detecting means and said subdividing means for discriminating scattering characteristics of specific elements and for outputting pulses indicative of the presence of said specific elements;
    a plurality of counting means corresponding to said plurality of discriminator means, each connected to said corresponding discriminator means for counting said output pulses from each of said discriminator means;
    counter resetting means for resetting each of said counting means; and
    means for outputting a predetermined reference signal indicative of an authentic document;
    comparison logic means for comparing the counted outputs of said counting means with said predetermined output corresponding to said predetermined reference signal.

2. An apparatus for examining a piece of paper having a pattern printed thereon, comprising:
    means for transferring said piece of paper;
    means for irradiating X-rays on said piece of paper transferred by said transferring means;
    detecting means for detecting fluorescent X-rays scattered from said printed pattern on said paper;
    subdividing means for subdividing said paper and the pattern located thereon into a plurality of areas;
    a plurality of discriminator means each connected to said detecting means and said subdividing means for discriminating scattering characteristics of specific elements and for outputting pulses indicative of the presence of specific elements;
    a plurality of rectifying circuit means corresponding to said plurality of discriminator means and each connected to said corresponding discriminator means for rectifying said output pulses from each of said discriminator means;
    a plurality of Schmitt trigger circuit means corresponding to said plurality of rectifying circuit means, each connected to said rectifying circuit means for detecting output pulses;
    Schmitt trigger level circuit fixer means, connected to the output of said corresponding Schmitt trigger circuit means for comparing the output of said Schmitt trigger circuit means with a presetvalue and for outputting a pulse when the output of said Schmitt trigger circuit means exceedes said preset level in said Schmitt level fixer means;

shift register means connected to said plurality of said Schmitt trigger level fixer means for storing the output of said plurality of Schmitt trigger level fixer means;

means for generating a predetermined reference signal indicative of an authentic document;

comparison judgement means connected to said shift register means for comparing the stored pattern contained within said shift level register means with said predetermined reference signal.

* * * * *